United States Patent [19]

Yoshida et al.

[11] Patent Number: 4,845,304
[45] Date of Patent: Jul. 4, 1989

[54] PROCESS FOR PRODUCING FLUOROBENZALDEHYDES

[75] Inventors: Yasuo Yoshida; Yoshikazu Kimura, both of Shizuoka, Japan

[73] Assignee: Ihara Chemical Industry Co., Ltd., Tokyo, Japan

[21] Appl. No.: 190,087

[22] Filed: May 4, 1988

[30] Foreign Application Priority Data

May 8, 1987 [JP] Japan .................................. 62-111978

[51] Int. Cl.$^4$ ...................... C07C 45/63; C07C 47/228
[52] U.S. Cl. ...................................... 568/433; 568/437
[58] Field of Search ................................. 568/433, 437

[56] References Cited

U.S. PATENT DOCUMENTS 4,218,567  8/1980  Manchand et al. ................. 568/433
4,446,075  5/1984  Eiglmeier et al. .................. 568/433

FOREIGN PATENT DOCUMENTS 074571  3/1983  European Pat. Off. ............ 568/437

*Primary Examiner*—J. E. Evans
*Assistant Examiner*—Karen E. Kulesza
*Attorney, Agent, or Firm*—Oblon, Spivak, McClelland, Maier & Neustadt

[57] ABSTRACT

A process for producing a fluorobenzaldehyde of the formula:

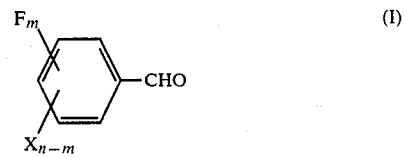

(I)

wherein X is a chlorine atom, a bromine atom or an iodine atom, n is an integer of from 1 to 5, and m is an integer of from 1 to 5, provided n≧m, which comprises reacting a halogenated benzaldehyde of the formula:

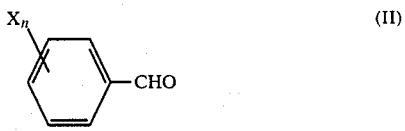

(II)

wherein X and n are as defined above, with a metal fluoride in the presence of a catalyst, wherein at least one member selected from the group consisting of quaternary phosphonium salts and quaternary ammonium salts is used as the catalyst.

13 Claims, No Drawings

PROCESS FOR PRODUCING FLUOROBENZALDEHYDES

The present invention relates to a process for producing fluorobenzaldehydes. More particularly, the present invention relates to a process for producing fluorobenzaldehydes useful as intermediates for agricultural chemicals or pharmaceuticals in good yield on an industrial scale by using commercially readily available starting materials.

In recent years, fluorine-containing agricultural chemicals or pharmaceuticals have been positively studied as they have excellent pharmacological or physiological activities. Fluorobenzaldehydes are known to be very important compounds as intermediates for the preparation of fluorine-containing agricultural chemicals or pharmaceuticals. For their production, it has been common to employ a method wherein firstly a fluorine atom is introduced into an aromatic ring, followed by introducing an aldehyde group by various means, such as a method of hydrolyzing a fluorobenzylidene chloride derived from a fluorotoluene (J. Chem. Soc., p. 5418–5421) (1961)) or a method of oxidizing a fluorobenzyl alcohol (J. Org. Chem., Vol. 48, p. 3126–3128 (1983)). However, such a production method has problems such that in the reaction to obtain a fluorine-containing aromatic compound to be used as the starting material, there is a danger in the operation, and treatment of the waste is difficult, and the starting material is hardly available. For these reasons, this method is not necessarily satisfactory for use as an industrial method.

On the other hand, it is well-known that in an aromatic compound having a strongly electron attractive group such as a nitro group or a cyano group at the o- or p-position to a halogen atom, the halogen atom can readily be substituted by fluorine by a reaction with a metal fluoride. However, in the case of a halogenated benzaldehyde in which such a strongly electron attractive group is absent, such substitution by fluorine is difficult, and the aldehyde group itself is reactive and likely to be converted into a carboxyl group and/or a hydroxyl group, whereby the desired product can scarcely be obtained. Thus, this method is not practical at all.

Accordingly, for the production of fluorobenzaldehydes, there has been no other choice than employing a method wherein a fluorine-containing compound is used as the starting material, although such a method has the above-mentioned problems. Under these circumstances, it has been desired to develop an industrially acceptable method.

It is an object of the present invention to provide a process for producing fluorobenzaldehydes in good yield on an industrial scale by using a readily available starting material and thus to satisfy such a desire.

The present inventors have conducted extensive researches to develop an industrial process for the production of fluorobenzaldehydes and, as a result, have found that by reacting a readily available halogenated benzaldehyde with a metal fluoride in the presence of a certain specific catalyst, it is possible to produce fluorobenzaldehydes in good yield while suppressing side reactions of the aldehyde group. It has been found also that the after-treatment can thereby be easily conducted, and thus this process is suitable for industrial application. The present invention has been accomplished on the basis of these discoveries.

The present invention provides a process for producing a fluorobenzaldehyde of the formula:

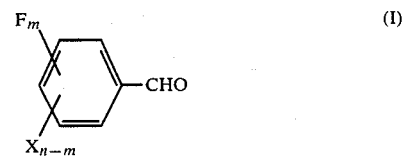

wherein X is a chlorine atom, a bromine atom or an iodine atom, n is an integer of from 1 to 5, and m is an integer of from 1 to 5, provided n≧m, which comprises reacting a halogenated benzaldehyde of the formula:

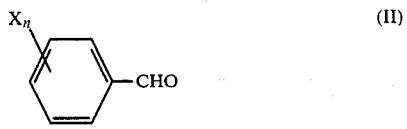

wherein X and n are as defined above, with a metal fluoride in the presence of a catalyst, wherein at least one member selected from the group consisting of quaternary phosphonium salts and quaternary ammonium salts is used as the catalyst.

Now, the present invention will be described in detail.

The halogenated benzaldehyde of the formula II which is used as a starting material in the present invention is a compound which is relatively readily available. In the formula, X is a chlorine atom, a bromine atom or an iodine atom, n is an integer of from 1 to 5, and when n is 2 or more, a plurality of X may be the same or different. Such a halogenated benzaldehyde includes, for example, monohalogenated benzaldehyde such as 2-chlorobenzaldehyde, 4-chlorobenzaldehyde or 2-bromobenzaldehyde, a dihalogenated benzaldehyde such as 2,4-dichlorobenzaldehyde, 3,4-dibromobenzaldehyde or 2-chloro-4-bromobenzaldehyde, a trihalogenated benzaldehyde such as 2,3,4-trichlorobenzaldehyde, 3,4,5-trichlorobenzaldehyde, 2,4,5-trichlorobenzaldehyde, 2,3,4-tribromobenzaldehyde or 3-bromo-4,5-dichlorobenzaldehyde, a tetrahalogenated benzaldehyde such as 2,3,4,6-tetrachlorobenzaldehyde or 2,3,4,5-tetrabromobenzaldehyde, and a pentahalogenated benzaldehyde such as 2,3,4,5,6-pentachlorobenzaldehyde or 2,3,4,5,6-pentabromobenzaldehyde.

Fluorobenzaldehydes obtainable from these halogenated benzaldehydes as starting materials are compounds represented by the above formula I, wherein X and n are as defined above with respect to the formula II, and m is an integer of from 1 to 5, provided m is the same or smaller than n. Usually, m is the same as n in the formula II, since it represents fluorine atoms in the fluorobenzaldehyde substituted for the halogen atoms in the starting material halogenated benzaldehyde.

However, when a polyhalogenated benzaldehyde is used as the starting material, it is possible to obtain a compound wherein m is smaller than n by controlling the amount of the metal fluoride reacted.

The quaternary phosphonium salts and the quaternary ammonium salts which may be used as the catalyst in the process of the present invention may be represented by the following formulas III and IV:

$$R^1R^2R^3R^4P^{\oplus}X'^{\ominus} \qquad (III)$$

$$R^1R^2R^3R^4N^{\oplus}X'^{\ominus} \qquad (IV)$$

wherein each of $R^1$, $R^2$, $R^3$ and $R^4$ which may be the same or different is an alkyl group, an aryl group or an aralkyl group, and $X'$ is a halogen atom. Specific examples of these compounds include tetramethylammonium chloride, tetramethylammonium bromide, tetraphenylphosphonium bromide, tetraphenylphosphonium chloride, triphenylmethylphosphonium bromide and triphenylmethylphosphonium chloride. Among them, quaternary phosphonium salts such as tetraphenylphosphonium bromide, tetraphenylphosphonium chloride, benzyltributylphosphonium chloride, benzyltriphenylphosphonium chloride and triphenylmethylphosphonium chloride are preferred.

In the present invention, the yield of fluorobenzaldehydes can further be improved by using as the catalyst a combination of at least one member selected from the above-mentioned quaternary phosphonium salts and quaternary ammonium salts and at least one member selected from the group consisting of crown ethers and polyalkylene glycols.

The crown ethers include, for example, 18-crown-6, dibenzo-18-crown-6, dicyclohexano-18-crown-6, 12-crown-4, 15-crown-5 and dibenzo-24-crown-8. Among them, 18-crown-6, dibenzo-18-crown-6 and dicyclohexano-18-crown-6 are preferred.

The polyalkylene glycols may be compounds represented by the formula:

$$R^6O(R^5O)_zR^7 \qquad (V)$$

wherein $R^5$ is an alkylene group, each of $R^6$ and $R^7$ which may be the same or different is a hydrogen atom, an alkyl group, an aryl group or an aralkyl group, and z is an integer of at least 2. Such compounds include, for example glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight: 300) dimethyl ether, polyethylene glycol (average molecular weight: 300) dibutyl ether, and polyethylene glycol (average molecular weight: 400) dimethyl ether. Among them, compounds wherein both $R^6$ and $R^7$ are alkyl groups, aryl groups or aralkyl groups are perferred.

In the present invention, the above-mentioned crown ethers or polyalkylene glycols may be used alone or in combination as a mixture of two or more, and the crown ethers and the polyalkylene glycols may be used in combination.

In the process of the present invention, when these crown ethers or polyalkylene glycols are used in combination with the above-mentioned quaternary phosphonium salts and quaternary ammonium salts as the catalyst, the member selected from the group of crown ethers and polyalkylene glycols is used in an amount of not more than 4 mols per mol of the member selected from the group consisting of the quaternary phosphonium salts and the quaternary ammonium salts. When crown ethers or polyalkylene glycols are used alone without the quaternary salts, the desired fluorobenzaldehydes are not substantially formed.

In the process of the present invention, the catalyst is used usually in an amount within a range of from 5 to 50 mol%, preferably from 10 to 40 mol%, relative to the halogenated benzaldehyde of the formula II.

In the process of the present invention, the reaction may be conducted in the absence of a solvent. However, if necessary, the raction may be conducted in the presence of a solvent. Solvents which may be employed include aprotic polar solvents such as dimethylformamide, dimethylsulfoxide and sulfolane, chlorobenzenes such as 1,2,4-trichlorobenzene, chlorotoluenes such as 3,4-dichlorotoluene, chloronaphthalenes such as 1-chloronaphthalene and alkyl-substituted naphthalenes such as 1-methylnapthalene and 2-methylnaphthalene. Among them, aromatic hydrocarbon solvents such as chlorobenzenes, chlorotoluenes, chloronaphthalenes and alkyl-substituted naphthalenes are preferred. Such a solvent is used usually in an amount within a range of from 100 to 1,000 g, preferably from 150 to 500 g, per mol of the halogenated benzaldehyde of the formula II.

The metal fluoride which may be used in the process for the present invention includes, for example, potassium fluoride and cesium fluoride. Particularly preferred is spray-dried potassium fluoride. Such a metal flouride is used usually in an amount of from 1 to 2 equivalent, relative to the halogen atoms to be substituted in the halogenated benzaldehyde of the formula II.

The reaction is conducted usually at a temperature within a range of from 150° to 300° C., preferably from 200° to 250° C. There is no particular restriction as to the reaction pressure, and the reaction may be conducted under atmospheric pressure or under an elevated pressure. When the reaction is conducted under an elevated pressure, the pressure is preferably not higher than 10 kg/cm². However, from the industrial point of view, it is preferred to conduct the reaction under atmospheric pressure. The reaction time is usually from 2 to 15 hours.

According to the process of the present invention, fluorobenzaldehydes can be produced in good yield by using readily available halogenated benzaldehydes as the starting material, and the after-treatment is easy, and further the recovery and reuse of the catalyst are possible. Thus, the process of the present invention is extremely valuable as an industrial process for the production of fluorobenzaldehydes.

The fluorobenzaldehydes obtained by the process of the present invention are useful as intermediates for fluorine-containing agricultural chemicals or pharmaceuticals.

Now, the present invention will be described in further detail wtih reference to Examples. However, it should be understood that the present invention is by no means restricted to such specific Examples.

EXAMPLE 1

Into a 100 ml four-necked flask equipped with a condenser and a mechanical stirrer, 8.7 g (150 mmol) of spray-dried potassium fluoride (manufactured by Morita Kagaku Kogyo K.K.), 4.2 g (10 mmol) of tetraphenylphosphonium bromide, 4.4 g (20 mmol) of tetraethylene glycol dimethyl ether, 20 g of 1-chloronaphthalene and 30 ml of toluene were introduced, and the mixture was heated and stirred in an oil bath to distill off toluene and to conduct azeotropic removal of water. The mixture was heated until the liquid temperature reached 150° C., and then the pressure in the interior of the reactor was reduced to a level of 45 Torr by a vacuum pump to distill off substantially all the remaining toluene. The content of the reactor was cooled to 100° C. and substituted by nitrogen gas. Then, 14.1 g (100 mmol) of 4-chlorobenzaldehyde was added thereto, and the mixture was stirred under nitrogen gas atmosphere at 210° C. for 7 hours.

After completion of the reaction, the reaction mixture was cooled and after an addition of 120 ml of dichloromethane, subjected to filtration to remove unreacted potassium fluoride and formed potassium chloride. After adding 1.0 g of cyclododecane as an internal standard, the filtrate was analyzed by gas chromatography, whereby it was found that 73% of 4-fluorobenzaldehyde was formed and 15% of 4-chlorobenzaldehyde remained. The selectivity for 4-fluorobenzaldehyde was 86%.

EXAMPLE 2

The operation was conducted in the same manner as in Example 1 except that 1.72 g (5.0 mmol) of polyethylene glycol (average molecular weight: 300) dimethyl ether was used instead of tetraethylene glycol dimethyl ether in Example 1. The filtrate thereby obtained was analyzed by gas chromatography, whereby it was found that 64% of 4-fluorobenzaldehyde formed, and 31% of 4-chlorobenzaldehyde remained. The selectivity for 4-fluorobenzaldehyde was 93%. Further, the dichloromethane solution after the post-treatment was concentrated and then subjected to distillation under a reduced pressure of 20 Torr to obtain 7.4 g of 4-fluorobenzaldehyde. Yield was 60%.

EXAMPLE 3

The operation was conducted in the same manner as in Example 1 except that tetraethylene glycol dimethyl ether as used in Example 1 was not used. The filtrate thus obtained was analyzed by gas chromatography, whereby it was found that 54% of 4-fluorobenzaldehyde formed and 43% of 4-chlorobenzaldehyde remained. The selectivity for 4-fluorobenzaldehyde was 95%.

EXAMPLE 4

The operation was conducted in the same manner as in Example 1 except that 20 g of sulfolane was used instead of 1-chloronaphthalene in Example 1. The filtrate thus obtained was analyzed by gas chromatography, whereby it was found that 49% of 4-fluorobenzaldehyde was formed and 5% of 4-chlorobenzaldehyde remained. The selectivity for 4-fluorobenzaldehyde was 52%.

EXAMPLE 5

A mixture comprising 8.7 g (150 mmol) of potassium fluoride, 4.2 g (10 mmol) of tetraphenylphosphonium bromide, 1.72 g (5 mmol) of polyethylene glycol (average molecular weight: 300) dimethyl ether and 20 g of 3,4-dichlorotoluene was subjected to dehydration treatment in the same manner as in Example 1, and then 14.1 g (100 mmol) of 4-chlorobenzaldehyde was added. The mixture was stirred at 210° C. and reacted for 5 hours.

After completion of the reaction, the reaction mixture was cooled and after an addition of an internal standard, analyzed by gas chromatography, whereby it was found that 75% of 4-fluorobenzaldehyde was formed.

EXAMPLE 6

A mixture comprising 17.4 g (0.3 mol) of potassium fluoride, 7.5 g (0.02 mol) of tetraphenylphosphonium chloride, 3.44 g (0.01 mol) of polyethylene glycol (average molecular weight: 300) dimethyl ether, 40 g of 1,3,4-trichlorobenzene and 28.2 g (0.2 mol) of 2-chlorobenzaldehyde was subjected to dehydration treatment in the same manner as in Example 1, and then the mixture was stirred at 210° C. and reacted for 7 hours.

After completion of the reaction, the reaction mixture was cooled and after an addition of an internal standard, analyzed by gas chromatography, whereby it was found that 52% of 2-fluorobenzaldehyde was formed and 45% of 2-chlorobenzaldehyde remained.

EXAMPLE 7

A mixture comprising 25 g (0.18 mol) of 4-chlorobenzaldehyde, 7.5 g (18 mmol) of tetraphenylphosphonium bromide, 3 g (9 mmol) of polyethylene glycol (average molecular weight: 300) dimethyl ether, 18.8 g (0.32 mmol) of potassium fluoride and 35 g of 1-methylnaphthalene was subjected to azeotropic dehydration with toluene in the same manner as in Example 1, and then the mixture was stirred at 210° C. for 7 hours.

After completion of the reaction, the reaction mixture was cooled and immediately subjected to distillation under reduced pressure to obtain 13.5 g of 4-fluorobenzaldehyde. The yield was 61%. The boiling point of this product was 73°–76° C./22 Torr (literature value, boiling point: 71°–73° C./15 Torr as disclosed in Nippon Kagaku Zasshi, Vol. 79, p. 1428 (1958)). The structure of the obtained product was identified by the NMR and MASS spectra to be the same as the authentic sample.

EXAMPLE 8

Into a three-necked flask equipped with a condenser and mechanical stirrer, 7.0 g (50 mmol) of 4-chlorobenzaldehyde, 4.4 g (75 mmol) of spray-dried potassium fluoride (manufactured by Laporte Chem.) 2,1 g (5 mmol) of tetraphenylphosphonium bromide and 1.3 g (5 mmol) of 18-crown-6 were introduced, and the mixture was stirred under a nitrogen gas atmosphere at 230° C. for 4.5 hours.

After completion of the reaction, the obtained reaction mixture was cooled, and after adding 50 ml of dichloromethane and 1.0 g of dibenzyl (internal standard) followed by stirring, analyzed by gas chromatography, whereby it was found that 75% of 4-fluorobenzaldehyde was formed and 6% of unreacted 4-chlorobenzaldehyde remained.

Further, the reaction mixture was filtered, and then dichloromethane was distilled off. The residue was distilled under reduced pressure to obtain 4.5 g (73%) of 4-fluorobenzaldehyde.

EXAMPLES 9 TO 14

The reactions were conducted under the same conditions as in Example 8 in the presence of various phase transfer catalysts, and the products were analyzed by gas chromatography. The results are shown in Table 1.

TABLE 1

| Example | Catalyst Type | Catalyst (mmol) | Yield of 4-fluorobenzaldehyde (%) | Unreacted 4-chlorobenzaldehyde |
|---|---|---|---|---|
| 9 | Ph$_4$PBr | 5 | 41 | 44 |
| 10 | Ph$_4$PCl | 5 | 43 | 21 |
| 11 | Ph$_4$PCl 18-CR-6 | 5 5 | 70 | 1 |
| 12 | Ph$_4$PBr CH$_3$O(CH$_2$CH$_2$O)$_4$CH$_3$ | 5 5 | 52 | 32 |
| 13 | Ph$_4$PBr CH$_3$O(CH$_2$CH$_2$O)$_4$CH$_3$ | 5 10 | 60 | 26 |
| 14 | Ph$_4$PBr PEG 300-Me$_2$ | 5 5 | 59 | 16 |

Note:
Ph$_4$PBr: Tetraphenylphosphonium bromide
Ph$_4$PCl: Tetraphenylphosphonium chloride
PEG 300-Me$_2$: Polyethylene glycol (average molecular weight: 300) dimethyl ether
18-CR-6: 18-Crown-6

COMPARATIVE EXAMPLE 1

The reaction was conducted in the same manner as in Example 8 except that tetraphenylphosphonium bromide as used in Example 8 was not added, and the product was analyzed by gas chromatography, whereby it was found that the yield of 4-fluorobenzaldehyde was 5%, and the unreacted rate was 86%.

COMPARATIVE EXAMPLE 2

The reaction was conducted in the same manner as in Example 12 except that tetraphenylphosphonium bromide as used in Example 12 was not added, whereby 4-fluorobenzaldehyde did not form at all.

EXAMPLE 15

The reaction was conducted in the same manner as in Example 8 except that 2-chlorobenzaldehyde was used instead of 4-chlorobenzaldehyde in Example 8, and the product was analyzed by gas chromatography, whereby it was found that the yield of 2-fluorobenzaldehyde was 68%, and the unreacted rate was 16%.

EXAMPLE 16

A mixture comprising 8.75 g (50 mmol) of 2,4-dichlorobenzaldehyde, 8.8 g (150 mmol) of spray-dried potassium fluoride, 3.15 g (7.5 mmol) of tetraphenylphosphonium bromide and 2.6 g (10 mmol) of 18-crown-6 was stirred at 230° C. for 7 hours under a nitrogen atmosphere.

The reaction solution was analyzed by gas chromatography, whereby the starting materials 2,4-dichlorobenzaldehyde and 2-chloro-4-fluorobenzaldehyde and 2-fluoro-4-chlorobenzaldehyde were not observed, and 2,4-difluorobenzaldehyde was the major product.

By distillation, 3.5 g of the product was isolated. This product has a boiling point of 62°–62° C./21 Torr, and the structure was confirmed to be 2,4-difluorobenzaldehyde. The yield was 49%.

EXAMPLE 17

The reaction was conducted at 230° C. for one hour by using 8.8 g (50 mmol) of 2,6-dichlorobenzaldhyde instead of 4-chlorobenzaldehyde in Example 8 and the same amount of the catalyst as used in Example 8.

The reaction solution was analyzed by gas chromatography, whereby 32% of the starting material 2,6-dichlorobenzaldehyde remained, 11% of 2,6-difluorobenzaldehyde and 41% of 2-chloro-6-fluorobenzaldehyde were formed.

EXAMPLE 18

The reaction was conducted in the same manner as in Example 17 except that 7.3 g (126 mmol) of spray-dried potassium fluoride was used and the reaction was conducted at 230° C. for 2.5 hours. Then, the reaction mixture was subjected to the same post-treatment as in Example 8, and by the distillation under reduced pressure, 8.9 g of 2,6-difluorobenzaldehyde having a boiling point of 84°–86° C./20 Torr was obtained. The yield was 69%.

EXAMPLE 19

The reaction was conducted at 230° C. for one hour by using 8.8 g (50 mmol) of 3,4-dichlorobenzaldehyde instead of 4-chlorobenzaldehyde in Example 8, 4.36 g (75 mmol) of spray-dried potassium fluoride and the same amount of the catalyst as used in Example 8.

The reaction mixture was subjected to the same post-treatment as in Example 1, and by the distillation under reduced pressure, 5.2 g of 3-chloro-4-fluorobenzaldehyde haivng a boiling point of 106°–119° C./22 Torr was obtained. The yield was 66%.

We claim:

1. A process for producing a fluorobenzaldehyde of the formula:

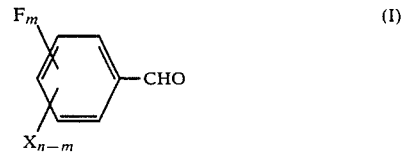
(I)

wherein X is a chlorine atom, a bromine atom or an iodine atom, n is an integer of from 1 to 5, and m is an integer of from 1 to 5, provided n≧m, which comprises reacting a halogenated benzaldehyde of the formula:

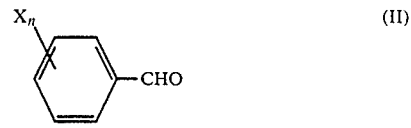
(II)

wherein X and n are as defined above, with a metal fluoride in the presence of a catalyst, wherein at least one member selected from the group consisting of quaternary phosphonium salts and quaternary ammonium salts is used as the catalyst.

2. The process according to claim 1, wherein a combination of at least one member selected from the group consisting of quaternary phosphonium salts and quaternary ammonium salts and at least one member selected from the group consisting of crown ethers and polyalkylene glycols, is used as the catalyst.

3. The process according to claim 2, wherein the reaction is conducted in the absence of a solvent.

4. The process according to claim 1, wherein a quaternary phosphonium salt is used as the catalyst.

5. The process according to claim 4, wherein the reaction is conducted in an aromatic hydrocarbon solvent.

6. The process according to claim 5, wherein the aromatic hydrocarbon solvent is a chlorinated benzene, a chlorinated toluene or a chlorinated naphthalene.

7. The process according to claim 5, wherein the aromatic hydrocarbon solvent is an alkyl-substituted naphthalene.

8. The process according to claim 5, wherein a combination of a quaternary phosphonium salt and at least one member selected from the group consisting of crown ethers and polyalkylene glycols, is used as the catalyst.

9. The process according to claim 2, wherein the member selected from the group consisting of crown ethers and polyalkylene glycols is used in an amount of not more than 4 mols per mol of the member selected from the group consisting of quaternary phosphonium salts and quaternary ammonium salts.

10. The process according to claim 8, wherein the member selected from the group consisting of crown ethers and polyalkylene glycols is used in an amount of not more than 4 mols per mol of the quaternary phosphonium salt.

11. The process according to claim 1, wherein the catalyst is used in an amount of from 5 to 50 mol% relative to the halogenated benzaldehyde of the formula II.

12. The process according to claim 1, wherein the catalyst is used in an amount of from 10 to 40 mol% relative to the halogenated benzaldehyde of the formula II.

13. The process according to claim 1, wherein the metal fluoride is potassium fluoride.

* * * * *